United States Patent
Grunewald et al.

(10) Patent No.: US 9,588,068 B2
(45) Date of Patent: Mar. 7, 2017

(54) COMBINATION NMR AND DIELECTRIC MEASUREMENT

(71) Applicant: VISTA CLARA INC., Mukilteo, WA (US)

(72) Inventors: Elliot D. Grunewald, Seattle, WA (US); David O. Walsh, Mukilteo, WA (US)

(73) Assignee: VISTA CLARA INC., Mukilteo, WA (US)

(*) Notice: Subject to any disclaimer, the term of this patent is extended or adjusted under 35 U.S.C. 154(b) by 523 days.

(21) Appl. No.: 14/160,243

(22) Filed: Jan. 21, 2014

(65) Prior Publication Data

US 2014/0203806 A1  Jul. 24, 2014

Related U.S. Application Data

(60) Provisional application No. 61/755,244, filed on Jan. 22, 2013.

(51) Int. Cl.
 *G01V 3/00* (2006.01)
 *G01N 24/08* (2006.01)
 *G01V 3/32* (2006.01)

(52) U.S. Cl.
 CPC ......... *G01N 24/084* (2013.01); *G01N 24/081* (2013.01); *G01V 3/32* (2013.01)

(58) Field of Classification Search
 USPC ....................................................... 324/309
 See application file for complete search history.

(56) References Cited

U.S. PATENT DOCUMENTS

| 4,710,713 | A | 12/1987 | Strikman |
| 5,233,522 | A | 8/1993 | Sinclair |
| 6,160,398 | A | 12/2000 | Walsh |
| 7,466,128 | B2 | 12/2008 | Walsh |
| 7,986,143 | B2 | 7/2011 | Walsh |
| 8,581,587 | B2 | 11/2013 | Walsh |
| 2004/0032257 | A1* | 2/2004 | Freedman ............... G01V 3/32 324/303 |
| 2004/0055745 | A1* | 3/2004 | Georgi ................... E21B 49/00 166/250.02 |
| 2011/0109311 | A1 | 5/2011 | Walsh |
| 2013/0187647 | A1 | 7/2013 | Walsh |
| 2013/0193969 | A1 | 8/2013 | Grunewald |
| 2013/0293228 | A1 | 11/2013 | Walsh |
| 2014/0009148 | A1 | 1/2014 | Walsh |
| 2014/0084927 | A1 | 3/2014 | Walsh |

(Continued)

OTHER PUBLICATIONS

Ajo-Franklin, "The dielectric properties of granular media saturated with DNAPL/water mixtures," Article, Geophysical Research Letters, vol. 31, 2004, 4 pages.

(Continued)

*Primary Examiner* — Rodney Fuller
(74) *Attorney, Agent, or Firm* — Jensen & Puntigam, P.S.; Nathaniel A. Gilder

(57) ABSTRACT

Technologies applicable to detection and characterization of subsurface contaminants by NMR and dielectric measurements are disclosed. The disclosed technologies include methods for obtaining and combining data from NMR and dielectric measurements to detect, quantify, and characterize non-native non-aqueous phase liquid (NAPL) contaminants located in geologic materials.

15 Claims, 6 Drawing Sheets

(56) References Cited

U.S. PATENT DOCUMENTS

| | | | | |
|---|---|---|---|---|
| 2014/0129149 A1* | 5/2014 | Gzara | G06F 17/00 | 702/11 |
| 2014/0229112 A1* | 8/2014 | Datey | E21B 47/00 | 702/7 |
| 2014/0320126 A1* | 10/2014 | Heaton | G01V 11/00 | 324/303 |
| 2014/0341455 A1* | 11/2014 | Cao Minh | G01V 3/32 | 382/131 |
| 2015/0094960 A1* | 4/2015 | Kadayam Viswanathan | G01V 11/00 | 702/13 |
| 2015/0219782 A1* | 8/2015 | Kadayam Viswanathan | G01V 3/32 | 324/309 |
| 2016/0047935 A1* | 2/2016 | Ali | G01V 3/32 | 702/7 |
| 2016/0061803 A1* | 3/2016 | Hadj-Sassi | E21B 43/00 | 324/309 |
| 2016/0130940 A1* | 5/2016 | Hsu | E21B 47/00 | 702/11 |

OTHER PUBLICATIONS

Bryar, "NMR relaxation measurements to quantify immiscible organic contaminants in sediments," Article, Water Resources Research, vol. 44, 2008, 10 pages.

Dunn, "Seismic Exploration vol. 32: Nuclear Magnetic Resonance Petrophysical and Logging Applications," Book, Pergamon, 2002, 253 pages.

Hedberg, "The Use of Nuclear Magnetic Resonance for Studying and Detecting Hydrocarbon Contaminants in Porous Rocks," Article, Water Resources Research, vol. 29, No. 4, 1993, 8 pages.

Hertzog, "Using NMR Decay-time Measurements to Monitor and Characterize DNAPL and Moisture in Subsurface Porous Media," Article, JEEG, Dec. 2007, 14 pages.

Huling, "Dense Nonaqueous Phase Liquids," Article, EPA, 1991, 21 pages.

Knight, "Rock/water interaction in dielectric properties: Experiments with hydrophobic sandstones," Article, Geophysics, vol. 60, 1995, 6 pages.

Knight, "The dielectric constant of sandstones, 60 kHz to 4 MHz," Article, Geophysics, vol. 52, 1987, 11 pages.

Tercier, "Effect of sorbed oil on the dielectric properties of sand and clay," Article, Water Resources Research, vol. 37, 2001, 12 pages.

* cited by examiner

1

COMBINATION NMR AND DIELECTRIC MEASUREMENT

CROSS REFERENCE TO RELATED APPLICATIONS

Priority is claimed to U.S. Provisional Patent Application No. 61/755,244, filed on 22 Jan. 2013, entitled "COMBINATION NMR AND DIELECTRIC MEASUREMENT," the disclosure of which is incorporated herein by reference in its entirety.

BACKGROUND

It is well-recognized in the field of environmental science that contamination of the subsurface by toxic substances is a significant problem. There exists a need for improved detection and characterization of underground contamination. In particular, it is known that non-aqueous phase liquid (NAPL) contaminants have been introduced into the subsurface by events such as pipeline leakages, improper waste disposal, and leaking storage tanks. These NAPL contaminants pose a significant hazard to human and environmental health. Because NAPL contaminants may be highly toxic, it is important to be able to detect and characterize instances of contamination that may affect groundwater so that appropriate remediation approaches may be developed.

SUMMARY

Technologies applicable to measurement and characterization of non-native NAPL contaminants underground through combined Nuclear Magnetic Resonance (NMR) and dielectric measurements are disclosed. Some example methods may comprise obtaining a measurement of NMR properties and a measurement of dielectric properties for a volume of the subsurface and combining the NMR and dielectric measurement data to determine the presence, quantity, and/or wetting state of non-native NAPL present in the formation in that subsurface volume.

Some example NMR measurement apparatus may include surface-based devices and/or downhole devices. The surface-based or downhole NMR devices may operate in the presence of Earth's geomagnetic field or may operate in the presence of elevated magnetic fields (e.g. produced by permanent magnets or electromagnets). Some example dielectric measurement devices may also include surface-based devices and/or in-situ sensor devices. In-situ dielectric devices may include dielectric or spectral induced polarization (SIP) logging devices, or crosshole radar devices. Surface-based dielectric devices may include Ground Penetrating Radar (GPR), Induced Polarization (IP), time-domain, or frequency domain dielectric devices.

DETAILED DESCRIPTION

Figure 1:
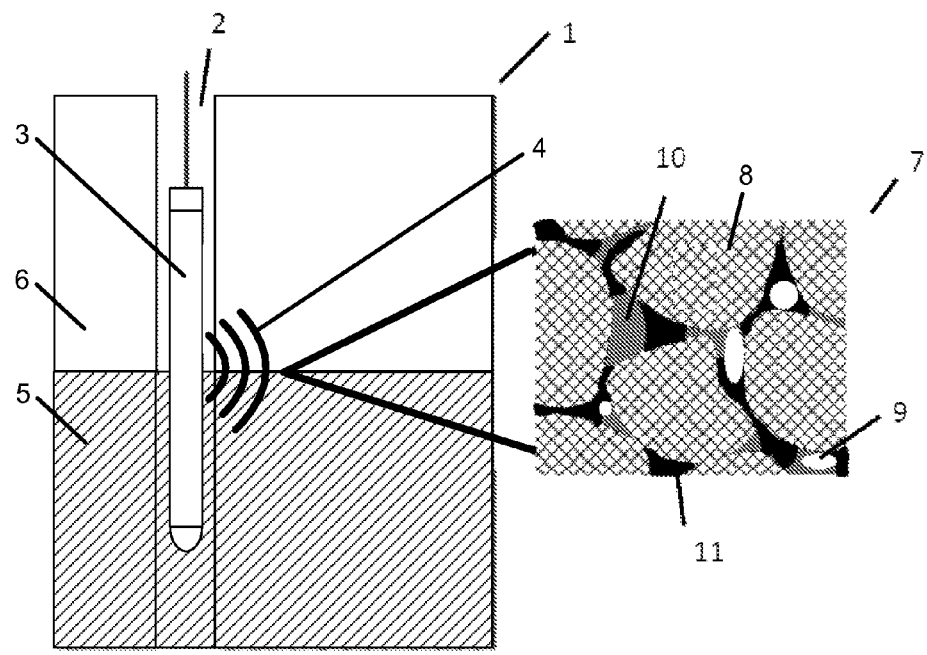
FIG. 1: graphical depiction of an Earth formation comprising NAPL and water saturated pore space in different wetting states, the Earth formation having a borehole and a sensor positioned in the borehole.

Prior to explaining embodiments of the invention in detail, it is to be understood that the invention is not limited to the details of construction or arrangements of the components and method steps set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

Technologies directed to measurement and characterization of non-native NAPL in the subsurface are disclosed. The attached figures illustrate technologies for obtaining a measurement sensitive to an NMR property of the subsurface and obtaining a measurement sensitive to a dielectric property of a subsurface volume and combining the measured data to detect and estimate quantities and properties of non-native NAPL present in the subsurface volume. NMR and dielectric measurements may include measurements with surface-based sensors or in-situ measurement devices. Properties of a non-native NAPL that may be estimated may include concentration, total volume, wetting-state, viscosity, chemical properties, and/or mobility.

NAPL contaminants may comprise, for example, common substances such as gasoline, creosote, and dry cleaning chemicals, and are classified based on their density relative to water: LNAPLs are lighter than water and DNAPLs are denser than water. In addition to being pervasive and highly toxic, NAPLs may also be difficult to characterize and remove from groundwater. This is because NAPLs may have a low solubility in water and at high concentrations may exist as an immiscible fluid phase separate from water. As such, the undissolved liquid phase may not readily flow with groundwater and can become trapped as isolated droplets or adsorbed to the grain surface. Although these immiscible fractions may be less mobile to flow, they may continue to release toxic levels of dissolved contamination into groundwater that can spread far from the source.

Site remediation may include accurate determination of NAPL concentrations, distribution, and wetting states. The wetting state may influence the mobility and migration of the contaminant. In a water-wet state, the NAPL may exist in the central pore volume as a fluid phase. In a NAPL-wetting state, the NAPL is sorbed to the grain surface. A mixed-wetting state can also exist between these end members. The pore-scale distribution of the contaminant and wetting state is controlled by various factors, including NAPL composition, organic soil fractions, and saturation history. Pore-scale distribution and wetting state of NAPL are important parameters to characterize in order to select optimal remediation and clean-up strategies.

Existing subsurface characterization methods do not adequately characterize the NAPL concentration, distribution, or wetting state. Fluid sampling can be used to measure concentrations of the dissolved contaminant fraction, however, the trapped immiscible and sorbed/wetting phases may not readily flow into the sampling well to be quantified. Core sampling can provide more direct access to this information, but has several drawbacks: samples are often inadvertently modified during extraction; further, drilling and coring is often prohibitively expensive and poses significant risks of spreading the contamination or exposing operators to health hazard. Many existing geophysical methods provide limited sensitivity to the presence of NAPL contaminants, and are instead more sensitive to other properties of the geologic formation such as electrical conductivity, magnetic susceptibility, or acoustic properties.

NMR methods and dielectric methods may be used to provide imaging and analysis of material samples. Geophysical NMR and dielectric measurement technologies may be used measure Earth materials using surface-based technologies and/or in-situ. For surface-based technologies, a measurement of a subsurface formation is performed non-invasively by a device at or above the ground surface. Surface-based dielectric technologies include, for example, GPR and IP, and SIP. Surface-based NMR technologies include, for example, Surface NMR (SNMR) technologies, magnetic resonance sounding technologies (e.g. as described in U.S. Pat. No. 7,466,128), and stray field technologies using elevated magnetic fields.

For "in-situ" sensor technologies, an apparatus is positioned in the subsurface to measure the formation surrounding the apparatus (e.g. as described in U.S. Pat. No. 4,710,713). Downhole logging technologies may be considered as a type of in-situ sensor technology. In example downhole logging technologies, an apparatus may be lowered into a borehole or well to measure the formation surrounding the apparatus. Downhole dielectric measurements may be performed using, for example, dielectric logging tools (U.S. Pat. No. 5,233,522), SIP logging tools, and cross-hole GPR tools. Downhole NMR logging technologies include, for example, Earth's field NMR logging tools, and pulsed NMR logging tools with permanent magnets.

In near-surface environments, the above technologies may be used to characterize groundwater aquifers. Surface-based and logging dielectric measurements may also provide sensitivity to NAPL contaminants in the shallow subsurface. In deep oil and gas investigations, these technologies are used to identify and characterize reservoirs containing natural hydrocarbons in order to ultimately produce economically valuable oil and gas resources.

FIG. 1 provides a graphical depiction of an Earth formation 1 with a borehole 2 and a sensor 3 positioned in the borehole. The sensor may provide either or both of NMR measuring capability and dielectric measuring capability in a measurement zone 4. The Earth formation may comprise NAPL and water saturated pore space in different wetting states. A bottom portion of the Earth formation below the water table 5 is shown with darker shading. A top portion of the Earth formation above the water table 6 is shown with lighter shading. FIG. 1 also provides an enlarged view of an example pore space 7 near the boundary between the top and bottom portions of the Earth formation. The enlarged example pore space contains grains 8 (hatched-shaded), air 9 (white), water 10 (dark shaded), and NAPL contaminant 11 (black shaded portions).

It is disclosed that NMR and dielectric measurements yield complementary information that may be exploited to obtain information about NAPL contamination. Referring to FIG. 1, one or more apparatus may be used to obtain NMR and dielectric measurements of a zone of the subsurface, such as the zone comprising the enlarged example pore space. The NMR data yield direct measurement of total fluid content, NMR relaxation times, and estimates of pore size distribution, fluid wetting state, and diffusion (related to fluid viscosity). Dielectric data, on the other hand, indicate the total water content and the water-wetted surface area, independent of the quantity of NAPL in the bulk pore fluid. Combining the data from the two types of measurement provides less ambiguous sensitivity to the NAPL concentration, and properties including wetting-state.

Figure 2:
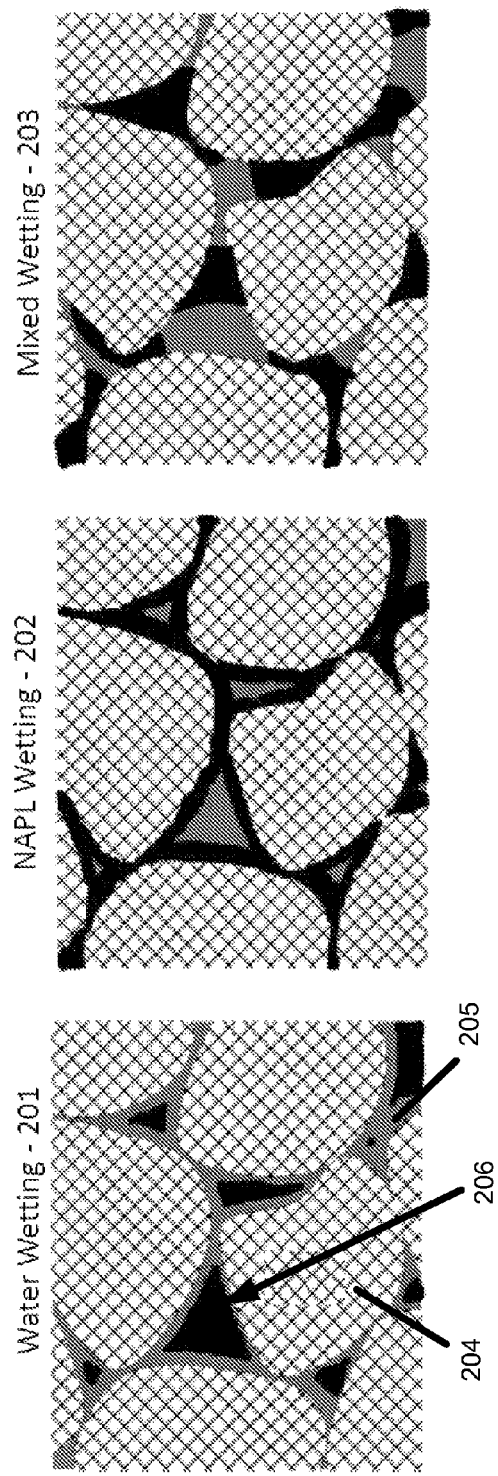
FIG. 2: a pore space with different wetting states of NAPL and water including a water wetting state, a contaminant wetting state, and a mixed wetting state.

FIG. 2 illustrates a pore space with different wetting states of NAPL and water including a water wetting state 201, a contaminant wetting state 202, and a mixed wetting state 203. As in FIG. 1, grains 204 are illustrated as hatched-shaded portions, water 205 is illustrated as darkly shaded portions, and NAPL contaminant 206 is illustrated as black shaded portions. The wetting state may influence the mobility and migration of the NAPL contaminant. In a water-wet state 201, the NAPL exists in the central pore volume as a fluid phase. In the NAPL-wetting state 202, the NAPL is sorbed to the grain surface. A mixed-wetting state 203 can also exist between water-wet states 201 and NAPL-wet states 202. The pore-scale distribution of the contaminant and wetting state may be controlled by various factors, including NAPL composition, organic soil fractions, and saturation history, and is one of the parameters to characterize when selecting optimal remediation strategies.

NMR Measurements

The NMR signal may be emitted directly by hydrogen nuclei in pore fluids. The signal amplitude indicates the total abundance of fluid hydrogen nuclei, which may correlate to the total abundance of water plus hydrocarbon or NAPL. Further, the NMR relaxation times $T_1$ and $T_2$ are sensitive to the pore-scale fluid environment. The magnitudes of the relaxation times provide sensitivity to fluid viscosity, pore-size distributions, and fluid wetting state. Fluids with a high viscosity (e.g. NAPL) generally undergo faster bulk-fluid relaxation and so exhibit a shorter value of $T_2$ than low-viscosity fluids (e.g. water). In most geologic materials, surface relaxation due to interactions between the fluid and grain interface dominates the $T_2$ response. Briefly, the surface relaxation rate can be estimated as $\rho S/V$ where $S/V$ is the ratio of the fluid-wetted surface area to fluid volume ratio in the pore space and $\rho$ is a parameter of the grain surface mineralogy. Fluids wetting the surface of small pores with a high surface-area-to-volume ratio exhibit shorter decay times than fluid in large pores, and fluids that wet the grain surface exhibit shorter decay times than those that are buffered from the grain surface. In heterogeneous systems where more than one type fluid or pore environment exists, the measurement yields a representative distribution of relaxation times. The NMR measurement can also be modified to determine the specific diffusion coefficient of the fluids contained in the pore space.

NMR measurements are sensitive to the presence and wetting-state of NAPL in contaminated soils, with certain limitations. Because both NAPL and water may contribute together to the NMR signal amplitude, there is a need to distinguish these two signals in some way from one another in order to characterize the NAPL independently. Sensitivity of NMR measurements to NAPL thus varies with factors including NAPL type and wetting conditions. For example, DNAPLs have a low hydrogen index and so exhibit distinctively lower NMR amplitude than water. LNAPLs, on the other hand, have a similar hydrogen index to water and so cannot be as readily distinguished. Under certain conditions water and NAPL may be distinguished based on relaxation times. Relaxation times of the saturating pore-fluid may increase when a second immiscible fluid wets the pore surface, thus buffering the saturating fluid from surface relaxation. For example, in a water-wet system, NAPL may be quantified if the long-$T_2$ NAPL signal is distinct from the short-$T_2$ water signal undergoing surface relaxation. However there is a practical difficulty of distinguishing different fluids and wetting-states using NMR measurements, in the absence of a priori knowledge of the bulk-fluid relaxation times and the surface relaxivity parameter $\rho$.

Dielectric Measurements

Measurement of the dielectric constant $\kappa$ reflects the extent to which a material can be polarized, and in geologic materials, $\kappa$ is sensitive to water content and the water-wetted surface area. The particular sensitivity varies as a function of measurement frequency as different polarization mechanisms become more or less dominant.

Figure 3:
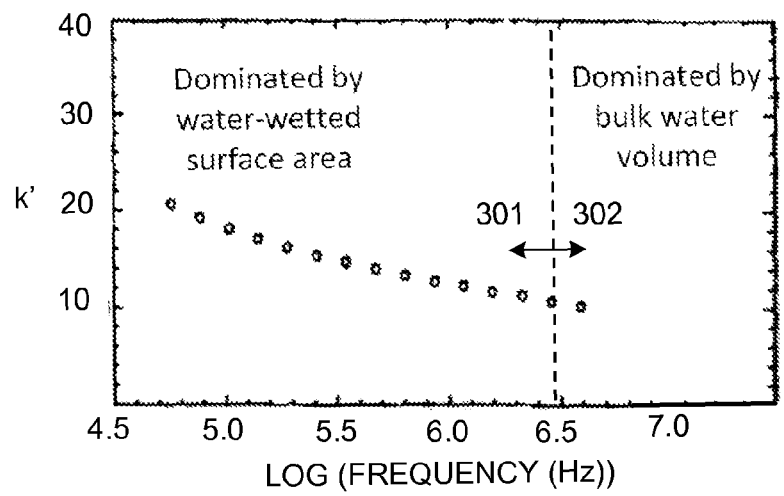
FIG. 3: Dielectric measurements on a water saturated sandstone as a function of frequency.

At high-MHz to GHz frequencies, the measurement is dominated by polarization of the water molecule. Water has a much higher dielectric constant ($\kappa\sim 80$) than other fluids such as oil ($\sim 2$) and the mineral phase ($\kappa\sim 6$-10). Thus at high frequency, measurements of $\kappa$ can be used to estimate water content using simple mixing laws such as the complex refractive index model (CRIM). At lower frequencies of kHz to low-MHz the dielectric measurement becomes dominated by polarization at the water-mineral interface via Maxwell-Wagner mechanisms. This increase in $\kappa$ at low frequencies is commonly referred to as dispersion and is illustrated in FIG. 3 for measurements in water-saturated sandstone, as demonstrated by Knight and Nur, 1987. The value of $\kappa$ is highest at low to kHz frequencies 301 where surface effects dominate and decreases at high frequencies, approaching a plateau at MHz frequencies 302 reflecting the bulk water volume. The magnitude of $\kappa$ at low frequencies and the slope of the dispersion curve both increase proportionally with the total surface area.

Figure 4:
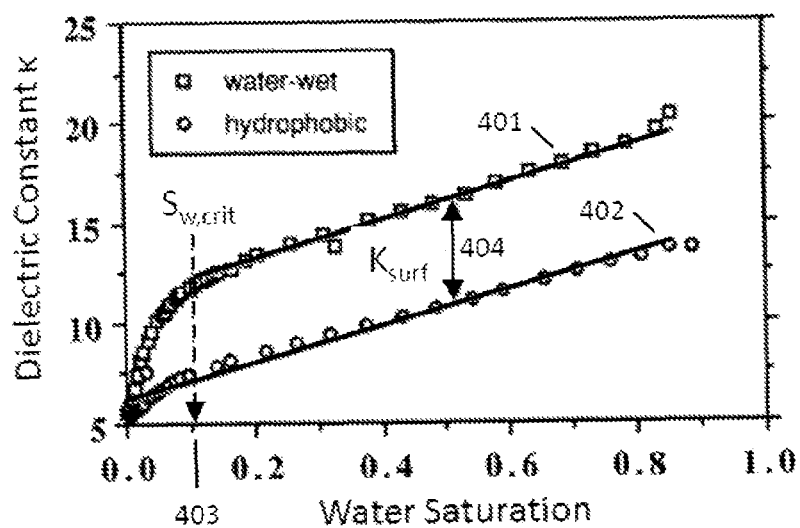
FIG. 4: Dielectric measurements 1 MHz for a water-wet and hydrophobic sandstone.

Furthermore, the surface influence at low frequencies may actually manifest only when the surface is water-wet. Shown in FIG. 4 is data from Knight and Abad (1995) which illustrates that $\kappa$ at 1 MHz may be much higher for a water-wetted sandstone (top curve 401) than when the same rock is made hydrophobic (bottom curve 402). For the hydrophobic rock 402, there may be a negligible surface influence and the magnitude of $\kappa$ may be accurately predicted as a function of the water content, using simple CRIM mixing laws. For the water-wet rock 401, the value of $\kappa$ may rise rapidly at low saturation, until the grain surface was fully wetted at critical saturation $S_{w,crit}$ 403. At higher saturations, $\kappa$ may follow the same slope as the hydrophobic curve, maintaining a static offset referred to here as $\kappa_{surf}$ 404. The magnitude of $\kappa_{surf}$ may be directly proportional to the water-wetted surface area.

Dielectric measurements may have value for characterizing NAPL contaminated systems. Using GHz frequencies, saturation of NAPL may be quantified in soils as the contaminant displaces water and lowers the observed dielectric constant. Such quantification may be possible in particular when total fluid content in the system is constant and known, when decreasing $\kappa$ may be attributed to increased NAPL saturation. It is not common, however, that these parameters are known a priori in the field. Sorption of oil to the grain surface of sands and clays may decrease the magnitude of $\kappa_{surf}$ at 10-100 kHz, and in particular, it may be possible to isolate surface effects from bulk-water given prior knowledge of the water content.

Thus, for practical site characterization, the dielectric measurement taken alone is sensitive to pore fluids and wetting state, but dielectric measurement contains ambiguity that can be resolved by incorporating other measurements.

Obtaining NMR and Dielectric Data

The present disclosure describes techniques for obtaining and combining dielectric and NMR data to detect and characterize non-native NAPL contaminants. The term "obtain" is here defined to mean obtaining data by any method. Data may be obtained by performing a measurement with an appropriate apparatus or may be obtained by collecting existing data from previously performed measurements. Apparatus for performing an NMR measurements may include surface-based devices and/or in-situ sensors. Surface-based NMR devices may include Earth's field surface NMR apparatus (U.S. Pat. No. 7,466,128) and/or devices that use an elevated static magnetic field. In-situ NMR devices may include NMR downhole logging devices (U.S. Pat. No. 4,710,713) and/or sensors that are installed in a more permanent manner in the formation. In-situ NMR devices may perform measurements using Earth's magnetic field and/or using elevated background magnetic fields (e.g. from permanent magnets or electromagnets).

Apparatus for performing a dielectric measurement may include surface-based devices and/or in-situ sensors. Dielectric measurement devices may derive estimates of the dielectric properties of an Earth formation for example by measuring how the formation influences an electric or electromagnetic field. Because the dielectric constant of a material is a frequency dependent property, dielectric measurement devices may be configured to measure the dielectric constant at a specific frequency or at multiple frequencies. Surface-based dielectric measurement devices may include IP measurements, where the induced potential between pairs of electrodes is measured, GPR measurements where the propagation of electromagnetic waves are measured, and/or other measurement methods that are sensitive to dielectric properties. In-situ dielectric measurement devices may include downhole logging devices (e.g. U.S. Pat. No. 5,233,522) and/or sensors that are installed in a more permanent manner in the formation (Zonge et al, 2005).

It is appreciated that some NMR or dielectric devices and measurement methods may not provide immediate or direct estimates of the NMR or dielectric properties for a specific volume of the subsurface. As an example, for an Earth's field SNMR measurement, multiple steps of processing including forwarding calculations of coil fields, data inversion, and multi-exponential fitting may be involved in transforming measured data into an estimated NMR property of a subsurface volume. Likewise a GPR multi-offset measurement may involve signal processing and inversion for a velocity model to determine the dielectric constant K. Even in-situ measurement may involve data processing and inversion to determine value of NMR parameters or K. These and other processing steps to transform measurements acquired with an NMR or dielectric apparatus into an estimate of a NMR or dielectric property of the subsurface may be performed in accordance with any NMR and/or dielectric measurement techniques known in the art.

Figure 5:
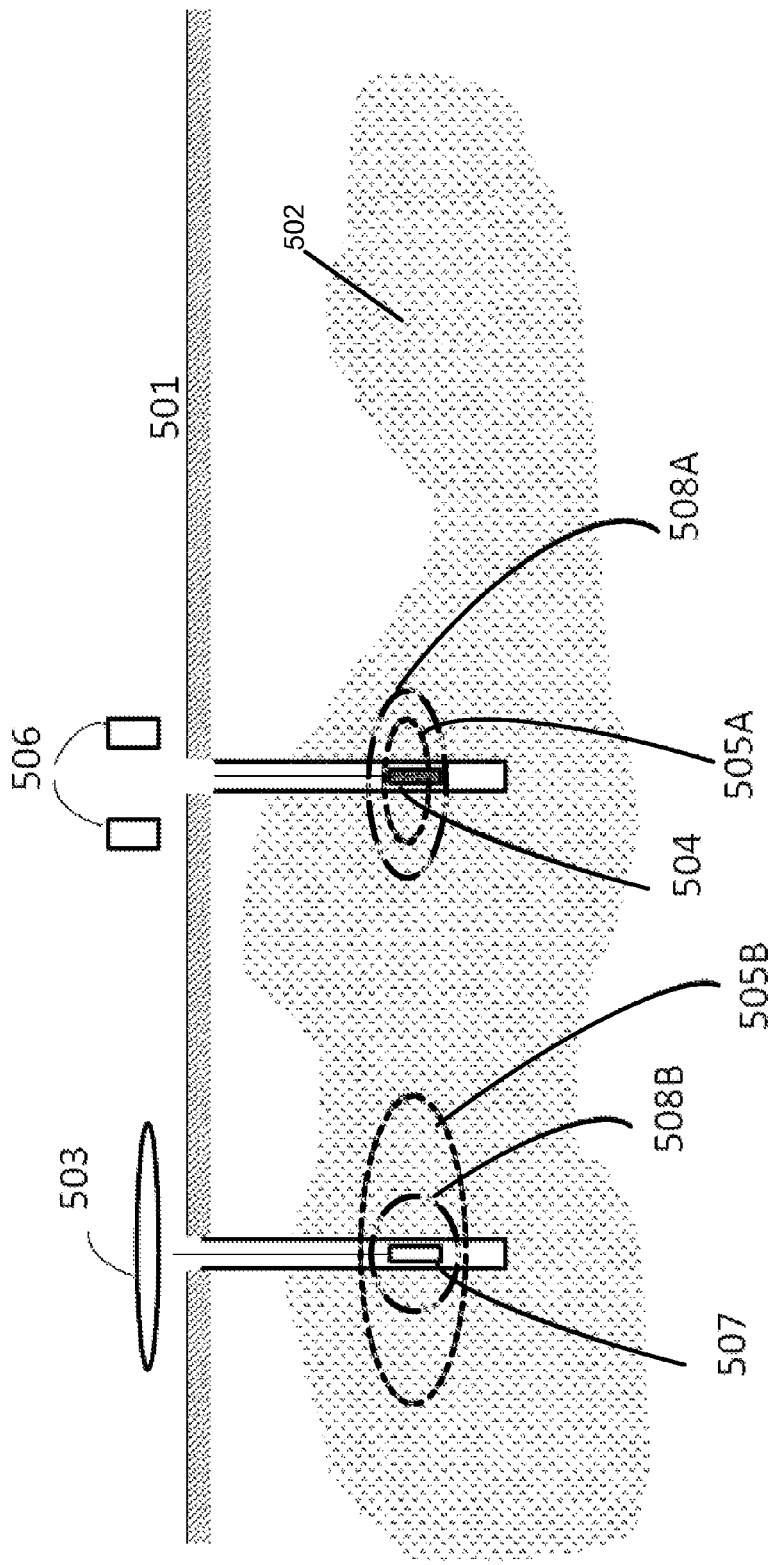
FIG. 5: Diagram showing an embodiment of obtaining NMR and dielectric measurements in a subsurface volume containing NAPL contamination.

FIG. 5 provides a diagram showing an embodiment of obtaining NMR and dielectric measurements in a subsurface volume containing NAPL contamination. Below the ground surface 501 there exists a volume containing non-native NAPL 502. NMR measurements may be obtained using surface-based apparatus 503, such as an Earth's field NMR device, or may be obtained using an in-situ sensor 504 such as an NMR logging tool. The NMR measurement may provide sensitivity to the NMR properties within a certain volume of the subsurface, e.g., NMR measurements by surface-based apparatus 503 may provide sensitivity to the NMR properties within a volume 505B underneath the surface-based apparatus 503, or NMR measurements by in-situ sensor 504 may provide sensitivity to the NMR properties within a volume 505A surrounding in-situ sensor 504.

Dielectric measurements may be obtained using surface-based apparatus 506, such as multi-offset GPR or may be obtained using an in-situ dielectric sensor 507 such as a dielectric logging tool. The dielectric measurement may provide sensitivity to the dielectric properties within a certain volume of the subsurface, e.g., dielectric measurements by surface-based apparatus 506 may provide sensitivity to the dielectric properties within the volume 508A surrounding in-situ NMR sensor 504, or dielectric measurements by in-situ dielectric sensor 507 may provide sensitivity to the dielectric properties within a volume 508B surrounding in-situ sensor 507. Other combinations of NMR and dielectric sensors may be used to obtain NMR and dielectric measurements of overlapping subsurface volumes, as will be appreciated with the benefit of this disclosure.

Combining NMR and Dielectric Data

This disclosure describes technologies for the detection and characterization of non-native NAPL in the subsurface. Non-native NAPL in the subsurface and techniques for detecting and characterizing it may be distinguished from naturally occurring oil and gas, and techniques for detecting and characterizing naturally occurring oil and gas. Applications of this disclosure may include characterizing NAPL contamination to support more effective and efficient remediation strategies. Embodiments of the invention may use both high and low frequency dielectric measurements to gain additional sensitivity properties of the NAPL and wetting state.

Figure 6:
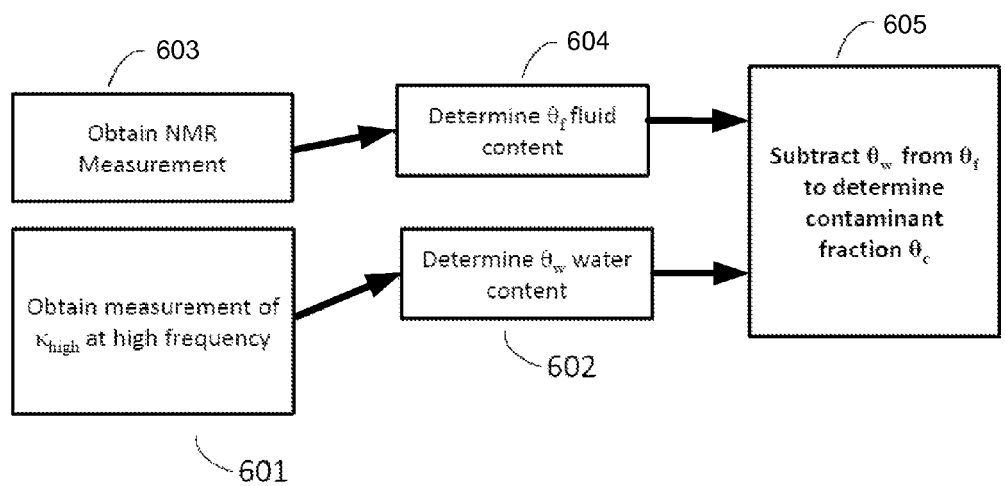
FIG. 6: Flowchart for integration of NMR and dielectric data by "Fluid Fractioning".
Figure 7:
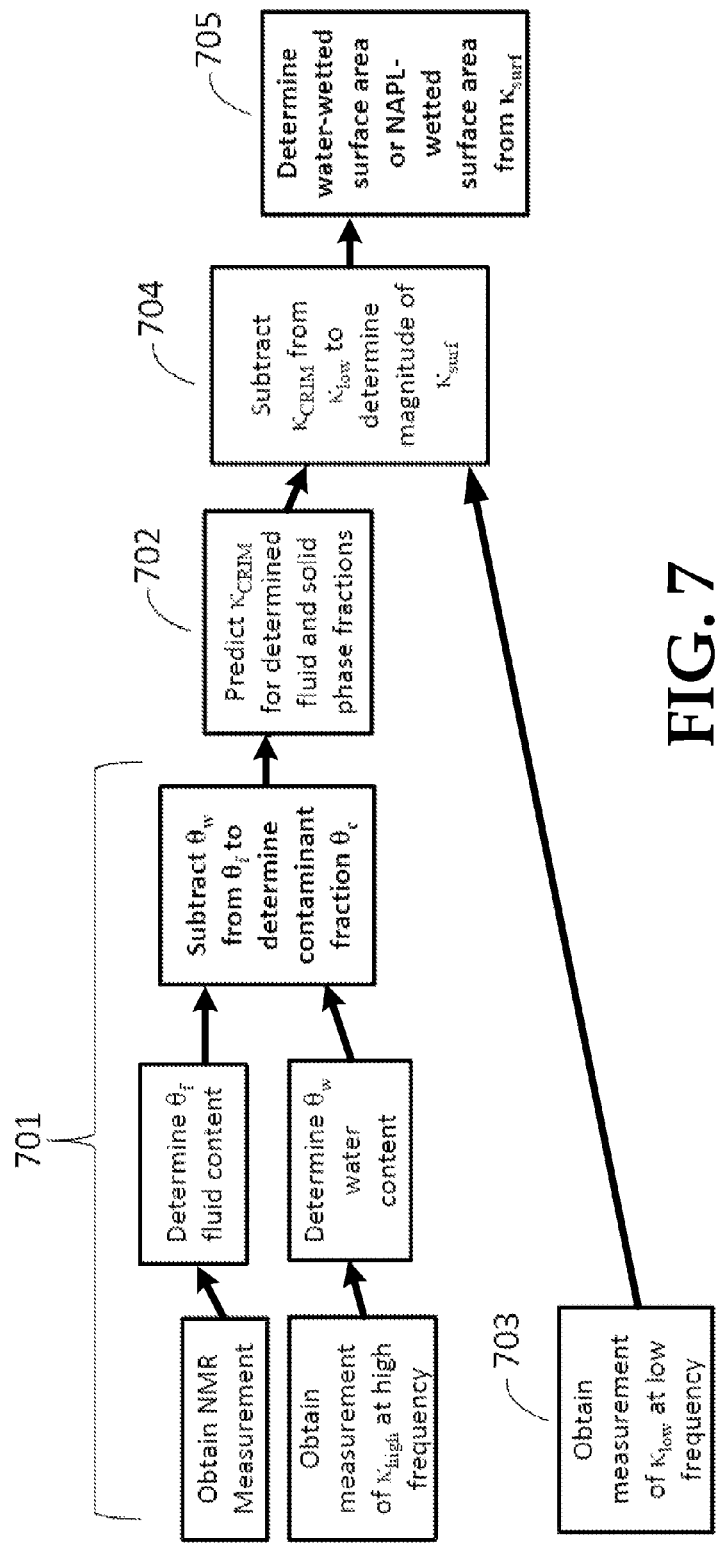
FIG. 7: Flowchart for integration of NMR and dielectric data by "Surface Isolation".

Given the complimentary nature of NMR and dielectric measurements, there are a number of approaches that may be taken to combine these data for NAPL characterization. FIG. 6 and FIG. 7 illustrate example methods to combine NMR and dielectric measurement data for NAPL characterization. It will be appreciated that some or all of the steps illustrated in FIG. 6 and FIG. 7 may optionally be carried out by one or more computers equipped with a processor, memory, and software adapted to cause the processor to perform the illustrated steps. It will also be appreciated that steps illustrated in FIG. 6 and FIG. 7 may be eliminated, combined, and/or re-arranged in some embodiments.

FIG. 6 illustrates embodiments of this disclosure that may be referred to as "fluid fractioning". In an embodiment of the fluid fractioning framework shown in FIG. 6, NMR measurements and high frequency dielectric measurements may be combined to quantify the volume of NAPL contaminant in a geologic material. Higher-frequency dielectric measurements may be obtained in a step 601, and a CRIM model may be used to determine the water volume fraction $\theta_w$ in a step 602. NMR measurements may also obtained in a step 603 and the signal amplitude may be used to directly determine the total fluid volume fraction $\theta_f$ in a step 604. Differencing the estimated water volume fraction and total fluid volume fraction in a step 605 may yield a straightforward estimate of the NAPL volume fraction (i.e. the fluid volume fraction that is not water).

A example advantage of the fluid-fractioning framework over independent NMR or dielectric measurements is that it may be effective in multi-phase environments when unknown quantities of air, solid, water, or NAPL phases are present, and does not require a priori knowledge of porosity. This framework may operate when substantial volumes of NAPL are present and allow quantification of NAPL saturation. This framework may be less sensitive when small volumes of NAPL are present.

Another embodiment of the disclosed interpretation framework appreciates the fact that even small amounts of NAPL wetting the grain surface are expected to have a large effect on low-frequency dielectric measurements. An embodiment that may be referred to as a "surface isolation framework" is illustrated in FIG. 7.

FIG. 7 illustrates a framework that may combine both high and low-frequency dielectric measurements in addition to NMR measurements to assess the surface wetting state. This workflow may begin using fluid fractioning in a step 701 to estimate the bulk fraction of water and NAPL, noting that for low concentrations the estimated bulk NAPL fraction may be close to zero. The estimated fluid fractions may be used in a step 702 to determine $\kappa_{CRIM}$, the value of $\kappa$ that would be predicted with no water-wetted surface (e.g. the hydrophobic blue curve in FIG. 3). CRIM or other mixing models for estimating $\kappa$ in the absence of surface effects may be used to determine this value. A low-frequency (e.g. less than 10 MHz) dielectric measurement may also be obtained in a step 703. The low-frequency dielectric measurement has combined sensitivity to both polarization of the bulk fluid (fluid effects) and to polarization of the water-wetted surface (surface effects). Subtracting the predicted KCRIM from the low-frequency measurement of $\kappa$ in a step 704 isolates the surface effect, yielding an estimate of the offset $\kappa_{surf}$. This estimate of $\kappa_{surf}$ may be used to estimate the amount of water-wetted surface area or sorbed NAPL in a step 705.

The advantage of this approach in FIG. 7 is that the surface wetting signature on $\kappa$ may be clearly separated from the bulk-water polarization signature, and thus does not require independent measurement of water or NAPL content. We note that the NMR relaxation time $T_2$ is also sensitive to the wetted surface area (i.e. $\rho S/V$) and the displacement of water by sorbed oil at the grain interface. NMR relaxation times, however, are also influenced by the relaxation rate of the bulk fluid (i.e. viscosity) and the grain mineralogy ($\rho$). Therefore the proposed surface isolation approach provides more reliable determination of the wetting-state. In other embodiments that framework may be adapted to include complimentary information from the NMR relaxation times that indicate wetting states.

There are various approaches by which apparatus and methods processes described herein can be implemented (e.g., hardware, software, and/or firmware), and the preferred approach may vary with the context in which the apparatus and methods are deployed. For example, if an implementer determines that speed and accuracy are paramount for operations of a computer or controller, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various embodiments have been disclosed herein, other aspects and embodiments will be apparent to those skilled in art.

The invention claimed is:

1. A combined Nuclear Magnetic Resonance (NMR) and dielectric measurement method, comprising:
    performing an NMR measurement of a subsurface volume with an NMR measurement device;
    using a measured signal amplitude, from the NMR measurement, to determine a total fluid volume fraction $\theta_f$ in the subsurface volume;
    performing a dielectric measurement of the subsurface volume with a dielectric measurement device;
    using a measured dielectric constant, from the dielectric measurement, to determine the water volume fraction $\theta_w$ in the subsurface volume;
    differencing the total fluid volume fraction $\theta_f$ and the water volume fraction $\theta_w$ in order to estimate a volume fraction of non-native Non-Aqueous Phase Liquid (NAPL) contamination contained in the subsurface volume; and
    selecting a remediation strategy for the non-native NAPL contamination contained in the subsurface volume based on the estimated volume fraction of non-native NAPL contamination.

2. The method of claim 1, further comprising:
    using a combination of the NMR measurement and the dielectric measurement to determine one or more of the total volume of the non-native NAPL contamination or the volumetric concentration of the non-native NAPL contamination.

3. The method of claim 1, wherein the NMR measurement device comprises a surface-based device or a downhole device.

4. The method of claim 1, wherein the dielectric measurement device comprises a surface-based device or a subsurface in-situ device.

5. The method of claim 4, wherein the dielectric measurement device comprises a Ground Penetrating Radar (GPR) device.

6. The method of claim 1, wherein the dielectric measurement of the subsurface volume is performed at multiple measurement frequencies, including at least one high frequency dielectric measurement above 10 MHz, and at least one low frequency dielectric measurement below 10 MHz.

7. The method of claim 1, further comprising:
    using the water volume fraction $\theta_w$ and an estimated volume fraction of non-native NAPL contamination to predict a value of a dielectric measurement in the subsurface volume in the absence of effects associated with polarization of the water-wetted surface;
    obtaining at least one low frequency dielectric measurement, less than 10 MHz, of dielectric properties of the subsurface volume;
    comparing the low frequency dielectric measurement to the predicted value of the dielectric measurement in the subsurface volume in the absence of effects associated with polarization of the water-wetted surface to derive an estimate of a low-frequency dielectric component associated with a water-wetted surface area.

8. The method of claim 7, further comprising:
    using the estimate of the low-frequency dielectric component associated with the water-wetted surface area to estimate the water-wetted surface area or a NAPL-wetted surface area.

9. The method of claim 1, wherein the non-native NAPL contamination comprises one or more of refined hydrocarbon fuels such as gasoline, tars such as creosote, or solvents such as dry cleaning chemicals.

10. The method of claim 1, wherein a mixing model is used to determine the water volume fraction $\theta_w$ in the subsurface volume from the measured dielectric constant.

11. The method of claim 1, further comprising using a combination of the NMR measurement and the dielectric measurement to determine wetting state of the non-native NAPL contamination, or to determine relative volume of non-native NAPL contamination wetting a grain surface and not wetting the grain surface.

12. The method of claim 1, further comprising using a combination of the NMR measurement and the dielectric measurement to determine a chemical composition of the non-native NAPL contamination.

13. The method of claim 1, wherein selecting the remediation strategy for the non-native NAPL contamination contained in the subsurface volume is furthermore based on one or more of a pore-size distribution in the subsurface volume and a wetting state of the non-native NAPL contamination.

14. A surface isolation framework method to measure Non-Aqueous Phase Liquid (NAPL) in a subsurface volume, comprising:
    using fluid fractioning to estimate a bulk fraction of water and NAPL in the subsurface volume;
    using the bulk fraction of water and NAPL in the subsurface volume to predict a value of a dielectric constant that would result if the subsurface volume had no water-wetted surface;
    performing a low-frequency dielectric measurement of the subsurface volume to obtain a low-frequency dielectric constant, wherein the low-frequency dielectric measurement has sensitivity to bulk fluid polarization and water-wetted surface polarization;
    subtracting the predicted value of the dielectric constant that would result if the subsurface volume had no water-wetted surface from the low-frequency dielectric constant to obtain an estimate of an offset dielectric constant; and
    using the offset dielectric constant to estimate an amount of water-wetted surface area or sorbed NAPL in the subsurface volume.

15. The method of claim 14, wherein the fluid fractioning to estimate a bulk fraction of water and NAPL in the subsurface volume comprises:
    performing an NMR measurement of the subsurface volume with an NMR measurement device;
    using a measured signal amplitude, from the NMR measurement, to determine a total fluid volume fraction $\theta_f$ in the subsurface volume;
    performing a dielectric measurement of the subsurface volume with a dielectric measurement device;
    using a measured dielectric constant, from the dielectric measurement, to determine the water volume fraction $\theta_w$ in the subsurface volume; and
    differencing the total fluid volume fraction $\theta_f$ and the water volume fraction $\theta_w$ in order to estimate a volume fraction of the NAPL contained in the subsurface volume.

* * * * *